United States Patent
Cheung et al.

(10) Patent No.: US 6,465,391 B1
(45) Date of Patent: Oct. 15, 2002

(54) SELECTIVE HYDROGENATION CATALYST AND PROCESSES THEREFOR AND THEREWITH

(75) Inventors: Tin-Tack Peter Cheung; Marvin M. Johnson, both of Bartlesville, OK (US)

(73) Assignee: Phillips Petroleum Company, Bartlesville, OK (US)

(*) Notice: Subject to any disclaimer, the term of this patent is extended or adjusted under 35 U.S.C. 154(b) by 4 days.

(21) Appl. No.: 09/643,266

(22) Filed: Aug. 22, 2000

(51) Int. Cl.[7] .......................... B01J 23/58; B01J 23/00; B01J 23/40; B01J 23/56; B01J 23/44
(52) U.S. Cl. ...................... 502/330; 502/325; 502/326; 502/327; 502/332; 502/333; 502/339
(58) Field of Search ................................. 502/325, 326, 502/327, 330, 332, 333, 339, 407, 415, 439, 347, 348; 501/133, 153; 585/259, 260, 261, 262

(56) References Cited

U.S. PATENT DOCUMENTS

| | | | | |
|---|---|---|---|---|
| 4,404,124 A | * | 9/1983 | Johnson et al. ......... 252/466 PT |
| 4,484,015 A | * | 11/1984 | Johnson et al. .............. 585/262 |
| 4,571,442 A | * | 2/1986 | Cosyns et al. .............. 585/261 |
| 4,960,647 A | * | 10/1990 | Grundy .................... 428/472.1 |
| 5,488,024 A | | 1/1996 | Cheung et al. ............. 502/325 |
| 5,489,565 A | * | 2/1996 | Cheung et al. ............. 502/325 |
| 5,510,550 A | * | 4/1996 | Cheung et al. ............. 585/259 |
| 5,518,556 A | * | 5/1996 | Weber et al. ............... 148/430 |
| 5,565,547 A | * | 10/1996 | Hefner et al. ............... 528/392 |
| 5,583,274 A | * | 12/1996 | Cheung et al. ............. 585/261 |
| 5,585,318 A | | 12/1996 | Johnson et al. ............. 502/330 |
| 5,866,735 A | * | 2/1999 | Cheung et al. ............. 585/273 |
| 5,889,187 A | | 3/1999 | Than et al. ................. 585/260 |
| 6,054,409 A | * | 4/2000 | Thanh et al. ............... 502/330 |
| 6,127,310 A | * | 10/2000 | Brown et al. ............... 502/339 |
| 6,204,218 B1 | * | 3/2001 | Flick et al. ................. 502/243 |

* cited by examiner

Primary Examiner—Stanley S. Silverman
Assistant Examiner—Cam N. Nguyen
(74) Attorney, Agent, or Firm—Charles W. Stewart

(57) ABSTRACT

A catalyst composition comprising an inorganic support material, a palladium component, a silver component, and a promoter component having the formula $XYF_n$, wherein X is an alkaline metal, Y is an element selected from the group consisting of antimony, phosphorus, boron, aluminum, gallium, indium, thallium, and arsenic, and n is an integer which makes $YF_n$ a monovalent anion. The catalyst is employed in the selective hydrogenation of acetylene. The catalyst is made by incorporating a palladium component, a silver component, and a promoter component into an inorganic support material.

17 Claims, 2 Drawing Sheets

SELECTIVE HYDROGENATION CATALYST AND PROCESSES THEREFOR AND THEREWITH

This invention relates to a new catalyst for the selective hydrogenation of acetylene as well as a method for making such catalyst and a method for selectively hydrogenating acetylene in admixture with ethylene.

BACKGROUND OF THE INVENTION

Ethylene is a monomer that is used in preparing a number of olefin polymers. Ethylene is generally made by the pyrolysis or catalytic cracking of refinery gas, ethane, propane, butane, and the like. Ethylene, so produced, usually contains small quantities of acetylene. In polymer grade ethylene, it is generally preferred that the acetylene content be less than 5 parts per million by weight (ppmw).

One technique that has been used in the past for reducing the amount of acetylene in a stream containing ethylene is to selectively hydrogenate the acetylene using a catalyst comprising an active alumina carrier, a palladium component, and a silver component. In such a hydrogenation process, it is desirable for substantially all of the acetylene to be converted to other hydrocarbons, preferably ethylene, while only an insignificant amount of the ethylene is converted.

The selective hydrogenation of acetylene from a feed containing ethylene is promoted by the presence of carbon monoxide in the feed. Although a variety of palladium-silver catalysts have proven to be effective for selectively hydrogenating acetylene in feeds containing relatively high concentrations of carbon monoxide, many of these same catalysts are ineffective when the feed contains low concentrations of carbon monoxide (for example, less than 5 ppmw).

Because certain commercial hydrocarbon streams that contain low concentrations of carbon monoxide and high concentrations of ethylene also contain acetylene, there exists a need to develop a catalyst and process for selectively hydrogenating acetylene in such a feedstream.

SUMMARY OF THE INVENTION

An object of this invention is to provide a method, and catalyst, for the treatment of a hydrocarbon stream comprising ethylene and acetylene whereby the acetylene is selectively and substantially consumed.

A further object of the present invention is to provide such a method and catalyst whereby acetylene in admixture with ethylene is hydrogenated to form a further amount of ethylene, without the concurrent consumption of a significant portion of ethylene.

Another object of the present invention is to provide a method and catalyst suitable for selectively hydrogenating acetylene in a feedstream which contains high concentrations of ethylene and low concentrations of carbon monoxide.

In accordance with a first embodiment of the present invention a catalyst composition is provided. Such catalyst composition comprises an inorganic support material, a palladium component, a silver component, and a promoter component. The promoter component has a formula $XYF_n$, wherein X is an alkaline metal, Y is an element selected from the group consisting of antimony, phosphorus, boron, aluminum, gallium, indium, thallium, and arsenic, and n is an integer which makes $YF_n$ a monovalent anion.

In a second embodiment of the present invention a process is provided. Such process comprises contacting, under acetylene hydrogenation conditions, a feed comprising ethylene and acetylene with the catalyst described in the first embodiment of the present invention.

In a third embodiment of the present invention a process for making a catalyst composition is provided. Such process comprises incorporating a palladium component, a silver component, and a promoter component, described in the first embodiment of the present invention, into an inorganic support.

DETAILED DESCRIPTION OF THE INVENTION

Figure 1:
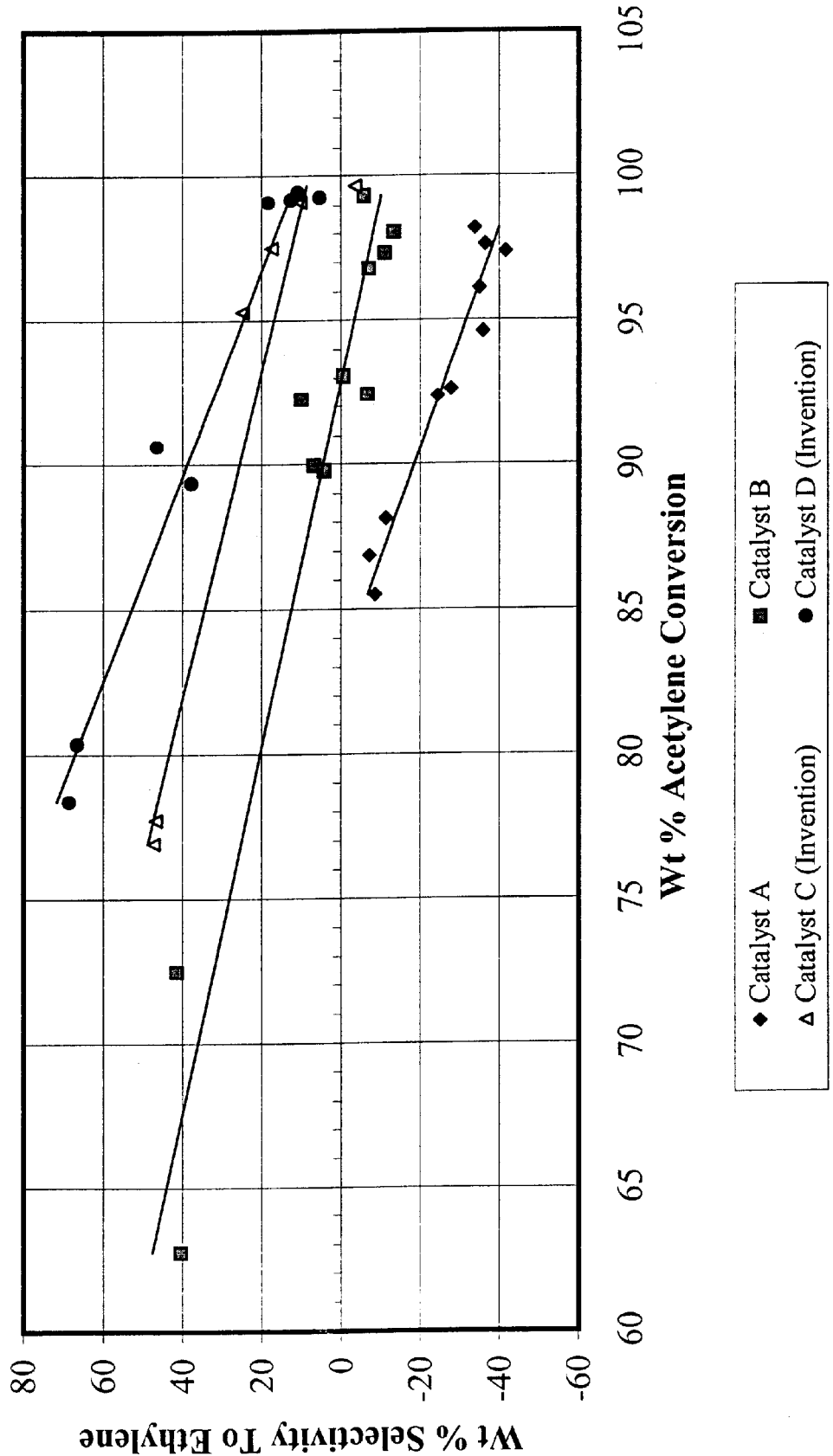
FIG. 1 is a plot of Weight Percent Acetylene Conversion versus Weight Percent Selectivity to Ethylene for the catalysts prepared in Example I and employed in the acetylene hydrogenation process of Example II.

The inventive composition of the first embodiment of the present invention comprises an inorganic support, a palladium component, a silver component, and a promoter component.

The inorganic support can be any inorganic solid support material suitable for use in a selective hydrogenation catalyst. Preferably, the inorganic support is selected from the group consisting of alumina, titania, zirconia, and mixtures thereof. The presently more preferred support material is alumina, most preferably alpha-alumina.

The palladium component can be palladium metal or palladium oxide. The amount of the palladium component present in the inventive composition can be any amount which provides a suitable acetylene hydrogenation catalyst. Preferably, the palladium component is present in the inventive composition in an amount which is from about 0.001 weight percent to about 1 weight percent by weight of the total catalyst composition. More preferably, the palladium component is present in an amount which is from about 0.005 weight percent to about 0.2 weight percent by weight of the total catalyst composition. Most preferably, the palladium component is present in an amount which is from 0.01 weight percent to 0.1 weight percent by weight of the total catalyst composition.

The silver component can be silver metal or silver oxide. The silver component can be present in any amount which provides a suitable acetylene hydrogenation catalyst. Preferably, the silver component is present in the inventive composition in an amount which is from about 0.001 weight percent to about 5 weight percent by weight of the total catalyst composition. More preferably, the silver component is present in an amount which is from about 0.005 weight percent to about 1 weight percent by weight of the total catalyst composition. Most preferably, the silver component is present in an amount which is from 0.01 weight percent to 0.5 weight percent by weight of the total catalyst composition.

The weight ratio of the silver component to the palladium component can be any ratio which provides a suitable acetylene hydrogenation catalyst. Preferably, the weight ratio of the silver component to the palladium component in the inventive composition is from about 1:1 to about 10:1. More preferably the weight ratio of the silver component to the palladium component is from 2:1 to 6:1.

The promoter component is a compound having the formula $XYF_n$, wherein X is an alkaline metal, Y is an element selected from the group consisting of antimony, phosphorus, boron, aluminum, galladium, indium, thallium, and arsenic, and n is an integer that makes $YF_n$ a monovalent anion. Preferably, X is an element selected from the group consisting of potassium, rubidium, and cesium, Y is an element selected from the group consisting of antimony and phosphorus, and n is an integer from 2 to 8 that makes $YF_n$ a monovalent anion. Most preferably, X is potassium, Y is antimony, and n is 6. Examples of suitable promoter components include $KPF_6$, $KSbF_6$, $KAsF_6$, $KBF_4$, $KAlF_4$, $KPF_6$, and $KSbF_6$, with $KSbF_6$ being the most preferred promoter component.

The amount of the promoter component present in the inventive catalyst composition can be any amount which provides a suitable acetylene hydrogenation catalyst. Preferably, the promotor component is present in the inventive composition in an amount such that the weight of X as a percentage of the total weight of the catalyst is from about 0.001 percent to about 10 percent, more preferably from about 0.01 percent to about 2 percent, and most preferably from 0.05 percent to 1 percent. The amounts of Y and F in the catalyst composition can be calculated using the amount of X, described above, and the structure of the promoter component, described above.

It is preferred for the palladium component to be distributed on the inorganic support as a "skin", with a high concentration of palladium being present near the surface of the support and a low concentration of palladium being present towards the center of the support. The silver and promoter components can be distributed evenly throughout the catalyst.

The inventive process of the second embodiment of the present invention comprises contacting a feed comprising ethylene and acetylene with the catalyst of the first embodiment of the present invention.

The feed preferably contains a high concentration of ethylene and a low concentration of acetylene. Preferably, the weight of ethylene as a percentage of the total weight of the feed is more than about 50 percent, more preferably more than about 80 percent, still more preferably more than about 90 percent, and most preferably more than 95 percent. Preferably, the weight of acetylene as a percentage of the total weight of the feed is less than about 50 percent, more preferably less than about 10 percent, still more preferably less than about 5 percent, and most preferably less than 2 percent.

An important feature of the present invention is its ability to selectively hydrogenate acetylene in a feedstream which contains small quantities of carbon monoxide. The amount of carbon monoxide present in the feed is preferably less than about 100 ppmw, more preferably less than about 20 ppmw, still more preferably less than about 5 ppmw, and most preferably less than 1 ppmw by weight of the total hydrocarbon feed. Typically, a minimum concentration of about 0.001 ppmw carbon monoxide is present in the feedstream.

Hydrogen can be present in the feed to promote the hydrogenation reaction. The amount of hydrogen employed can be an amount which provides a molar ratio of hydrogen to acetylene of from about 0.1:1 to about 100:1, more preferably from about 0.05:1 to about 20:1, most preferably from 1:1 to 5:1.

The feed may contain small amounts of various compounds other than ethylene, acetylene, hydrogen, and carbon monoxide (such as, for example, methane, ethane, propane, propene, butane, butenes, and hydrogen sulfide); however, it is preferred that the total amount of compounds other than ethylene, acetylene, hydrogen, and carbon monoxide in the feed is minimized such that the total weight of such other compounds as a percentage of the total weight of the feed is less than about 50 percent, more preferably less than about 10 percent, still more preferably less than about 5 percent, and most preferably less than 2 percent.

The reaction conditions employed in carrying out the acetylene hydrogenation process of the present invention can be any conditions which are effective to selectively hydrogenate acetylene. The temperature employed in the selective hydrogenation process of the present invention depends largely on the activity of the catalyst composition. Generally, a reaction temperature in the range of from about 40° C. to about 200° C. is employed. Preferably, the reaction temperature is from about 60° C. to about 150° C. Any suitable reaction pressure can be employed. Generally, the total pressure is in the range of from about 100 psig to about 1000 psig. The gas hourly space velocity (GHSV) of the feed can also vary over a wide range. Typically, the GHSV will be in the range of from about 1000 to about 10,000 $m^3$ of feed per $m^3$ of catalyt per hour, more preferably from about 2000 to about 8000 $m^3/m^3/hr$.

It is desirable for the hydrogenated product stream produced by the selective hydrogenation process of the present invention to be substantially acetylene-free. Preferably, the hydrogenated product stream contains acetylene in an amount such that the weight of acetylene as a percentage of the total weight of the hydrogenated product stream is less than about 1 percent, preferably less than about 0.5 percent, still more preferably less than about 0.1 percent, and most preferably less than about 0.05 percent.

The substantially acetylene free hydrogenated product stream is produced by converting substantially all the acetylene present in the feed into other compounds. Preferably, the weight of acetylene converted to other compounds as a percentage of the total weight of the acetylene present in the feed is more than about 50 percent, more preferably more than about 80 percent, still more preferably more than about 90 percent, and most preferably more than about 95 percent.

It is preferred for a substantial amount of the acetylene present in the feed to be converted to ethylene, as opposed to other compounds. Preferably, the weight of acetylene converted to ethylene as a percentage of the weight of the total acetylene converted is greater than about 20 percent, more preferably greater than about 40 percent, and most preferably greater than 50 percent.

It is also preferred in carrying out the process of the present invention that the amount of ethylene consumed by hydrogenation be minimized. Preferably, less than 10 weight percent of the ethylene in the feed is consumed. More preferably, less than 3 weight percent of the ethylene is consumed. Still more preferably, less than 1 weight percent of the ethylene is consumed. Most preferably, less than 0.5 weight percent of the ethylene is consumed.

The inventive process of the third embodiment of the present invention is a method for making a catalyst composition comprising an inorganic support, a palladium component, a silver component, and a promoter component. The quantities and identity of the inorganic support, palladium component, silver component, and promoter component in the catalyst produced by the process of the present embodiment are those described in the first embodiment of the present invention.

The palladium, silver, and promoter components can be incorporated into the inorganic alumina support using any suitable method known in the art that will yield a catalyst composition meeting the above-described parameters. The presently preferred technique involves impregnating the alumina support using an aqueous solution or solutions of the components. The alumina support can be simultaneously impregnated using an aqueous solution containing a palladium component, the silver component, and the promoter component. It is preferred, however, for the impregnation of the support with each component to be performed separately.

The preferred aqueous solution used to impregnate the alumina support with the palladium component comprises palladium chloride. The preferred aqueous solution used to impregnate the alumina support with the silver component comprises silver nitrate. The preferred aqueous solution used to impregnate the alumina support with the promoter component comprises a promoter component selected from the group consisting of potassium hexafluorophosphate, potassium hexafluoroantimonate, potassium hexafluoroarsenate, potassium tetrafluoroborate, potassium tetrafluoroarsenate, and potassium hexafluoroaluminate. Most preferably, the aqueous solution used to impregnate the alumina support with the promoter component comprises potassium hexafluoroantimonate.

The catalyst may be dried or calcined, or both, after each impregnation, or after all impregnations have been performed. The calcining can be performed at temperatures of from about 100° C. to about 600° C., preferably from about 150° C. to about 450° C.

The calcining is preferably followed by a reduction step. The reduction step can be accomplished using the feed for the selective hydrogenation process and/or hydrogen. Preferably, the reduction step is practiced in accordance with the wet reduction process taught in U.S. Pat. No. 5,510,550, the disclosure of which is incorporated by reference herein.

The following examples are provided to help illustrate the invention, but they are not intended to limit the scope of the invention.

EXAMPLE I

This example illustrates the preparation of supported palladium/silver catalysts to be used for acetylene hydrogenation.

Catalyst A, which was a Pd/Ag/Al$_2$O$_3$ catalyst containing 0.02 weight percent palladium, 0.13 weight percent silver, 0.33 weight percent potassium as potassium fluoride, and about 99 weight percent alumina, was prepared by reducing 50 grams of the catalyst in hydrogen flowing at 200 cc/m at 1 atmosphere and 200° C. for 3 hours.

Catalyst B was prepared by reducing 50 grams of a commercial Pd/Ag/Al$_2$O$_3$ catalyst in hydrogen flowing at 200 cc/m at 1 atmosphere and 194° C. for about 3 hours. The commercial catalyst was provided by United Catalysts Incorporated (UCI), Louisville, Ky., under the product designation of "G-83C" and contained 0.023 weight percent palladium, 0.065 weight percent silver, and about 99 weight percent alumina.

Catalyst C (invention) was prepared by impregnating 25.02 grams of G-83C (UCI) commercial catalyst with a solution of 0.0621 grams KPF$_6$ in 7.18 grams of water, followed by drying at 105° C. for several hours and calcining in air at 377° C. for 1 hour.

Catalyst D (invention) was prepared by impregnating 50.16 grams of G-83C (UCI) commercial catalyst with a solution of 0.1844 grams KSbF$_6$ in 13.4 grams of water, followed by drying at ambient temperature, and calcining in air at 400° C. for about 4 hours.

EXAMPLE II

This example illustrates the effectiveness of Catalysts A–D for selectively hydrogenating acetylene in feeds containing ethylene.

The acetylene hydrogenation tests were carried out as follows. About 20 cc of Catalysts A–D was placed in a stainless steel reactor tube having a 0.5 inch inner diameter and a length of about 18 inches. Prior to charging the hydrogenation feed to the reactor, Catalysts A–D were reduced in hydrogen flowing at 50 cc/m. Catalyst A was reduced at 1 atmosphere and 136° F. for 1½ hours. Catalyst B was reduced at 1 atmosphere and 188° F. for 1 hour. Catalyst C was reduced at 100 psig and 131° F. for 2 hours. Catalyst D was reduced at 1 atmosphere and 143° F. for 1½ hours.

After reduction with hydrogen, a feed containing ethylene and acetylene was introduced into the reactor tube at a rate of about 900 cc/min. The compositions of the feeds used to test Catalysts A and D were the same, and the compositions of the feeds used to test Catalysts B and C were the same. Hydrogen was added to the feed in an amount such that the molar ratio of hydrogen to acetylene was 1.8. The reactor temperature was gradually increased to the desired reaction temperature, and samples of the formed product were analyzed by means of gas chromatograph at various time intervals.

Tables A–D present reaction temperatures, feed compositions, acetylene conversions and selectivities for the selective acetylene hydrogenation tests employing Catalysts A–D.

TABLE A

| | | CATALYST A | | | | | | | | | |
|---|---|---|---|---|---|---|---|---|---|---|---|
| Stream | Feed | Product Run #1 | Product Run #2 | Product Run #3 | Product Run #4 | Product Run #5 | Product Run #6 | Product Run #7 | Product Run #8 | Product Run #9 | Product Run #10 |
| Reaction Temp. (F.) | — | 88 | 88 | 91 | 94 | 100 | 101 | 101 | 107 | 111 | 116 |
| Wt % Acetylene | 1.26 | 0.18 | 0.17 | 0.15 | 0.10 | 0.09 | 0.07 | 0.05 | 0.03 | 0.03 | 0.02 |
| Wt % Ethlylene | 95.22 | 95.13 | 95.14 | 95.10 | 94.94 | 94.90 | 94.79 | 94.80 | 94.77 | 94.71 | 94.80 |
| Wt % Ethane | 0 | 0.87 | 0.95 | 0.96 | 1.19 | 1.25 | 1.31 | 1.36 | 1.36 | 1.39 | 1.32 |
| Wt % C1 | 3.50 | 3.56 | 3.46 | 3.52 | 3.49 | 3.52 | 3.52 | 3.50 | 3.52 | 3.55 | 3.54 |
| Wt % C4 | 0 | 0.13 | 0.14 | 0.14 | 0.15 | 0.15 | 0.15 | 0.16 | 0.16 | 0.16 | 0.16 |
| Wt % C4+ | 0 | 0.26 | 0.28 | 0.28 | 0.29 | 0.24 | 0.30 | 0.29 | 0.31 | 0.32 | 0.32 |
| % Acet. conversion | — | 85.51 | 86.86 | 88.12 | 92.40 | 92.64 | 94.62 | 96.12 | 97.62 | 97.39 | 98.18 |
| % Sel. to Ethlyene | — | −8.65 | −7.14 | −11.38 | −24.40 | −27.73 | −35.86 | −34.96 | −36.44 | −41.64 | −33.74 |

TABLE B

CATALYST B

| Stream | Feed | Product Run #1 | Product Run #2 | Product Run #3 | Product Run #4 | Product Run #5 | Product Run #6 | Product Run #7 | Product Run #8 | Product Run #9 | Product Run #10 | Product Run #11 |
|---|---|---|---|---|---|---|---|---|---|---|---|---|
| Reaction Temp. (F.) | — | 118 | 121 | 128 | 128 | 129 | 129 | 132 | 136 | 138 | 142 | 144 |
| Wt % Acetylene | 1.13 | 0.31 | 0.42 | 0.11 | 0.09 | 0.08 | 0.09 | 0.12 | 0.04 | 0.03 | 0.02 | 0.01 |
| Wt % Ethlylene | 92.67 | 98.01 | 97.96 | 97.74 | 97.60 | 97.66 | 97.77 | 97.71 | 97.59 | 97.55 | 97.52 | 97.60 |
| Wt % Ethane | 0 | 0.30 | 0.30 | 0.71 | 0.86 | 0.82 | 0.69 | 0.74 | 0.92 | 0.97 | 1.00 | 0.96 |
| Wt % C1 | 1.17 | 1.14 | 1.14 | 1.15 | 1.16 | 1.15 | 1.15 | 1.15 | 1.15 | 1.15 | 1.15 | 1.15 |
| Wt % C4 | 0 | 0.11 | 0.09 | 0.13 | 0.13 | 0.13 | 0.13 | 0.12 | 0.14 | 0.14 | 0.13 | 0.14 |
| Wt % C4+ | .04 | 0.24 | 0.19 | 0.28 | 0.29 | 0.29 | 0.29 | 0.27 | 0.29 | 0.29 | 0.29 | 0.28 |
| % Acet. conversion | — | 72.49 | 62.73 | 89.97 | 92.46 | 93.08 | 92.28 | 89.80 | 96.81 | 97.34 | 98.05 | 99.33 |
| % Sel. to Ethlyene | — | 41.63 | 40.48 | 6.95 | −6.60 | −0.41 | 10.15 | 4.39 | −6.98 | −11.05 | −13.33 | −5.75 |

TABLE C

CATALYST C (Invention)

| Stream | Feed | Product Run #1 | Product Run #2 | Product Run #3 | Product Run #4 | Product Run #5 | Product Run #6 |
|---|---|---|---|---|---|---|---|
| Reaction Temp. (F.) | — | 135 | 140 | 151 | 158 | 164 | 178 |
| Wt % Acetylene | 1.13 | 0.26 | 0.25 | 0.05 | 0.03 | 0.01 | 0.00 |
| Wt % Ethlylene | 97.67 | 98.08 | 98.08 | 97.94 | 97.86 | 97.78 | 97.63 |
| Wt % Ethane | 0 | 0.28 | 0.28 | 0.59 | 0.69 | 0.80 | 0.96 |
| Wt % C1 | 1.17 | 1.15 | 1.15 | 1.15 | 1.15 | 1.15 | 1.15 |
| Wt % C4 | 0 | 0.10 | 0.11 | 0.12 | 0.13 | 0.14 | 0.14 |
| Wt % C4+ | .04 | 0.23 | 0.24 | 0.26 | 0.26 | 0.27 | 0.27 |
| % Acet.e conversion | — | 76.93 | 77.73 | 95.30 | 97.52 | 99.11 | 99.65 |
| % Sel. to Ethlyene | — | 47.41 | 46.81 | 24.99 | 17.47 | 10.28 | −3.52 |

TABLE D

CATALYST D (Invention)

| Stream | Feed | Product Run #1 | Product Run #2 | Product Run #3 | Product Run #4 | Product Run #5 | Product Run #6 | Product Run #7 | Product Run #8 |
|---|---|---|---|---|---|---|---|---|---|
| Reaction Temp. (F.) | — | 126 | 129 | 137 | 140 | 144 | 146 | 151 | 152 |
| Wt % Acetylene | 1.26 | 0.25 | 0.27 | 0.13 | 0.12 | 0.01 | 0.01 | 0.01 | 0.01 |
| Wt % Ethlylene | 95.22 | 95.90 | 95.90 | 95.65 | 95.76 | 95.45 | 95.38 | 95.36 | 95.29 |
| Wt % Ethane | 0 | 0.00 | 0.00 | 0.31 | 0.22 | 0.61 | 0.67 | 0.69 | 0.74 |
| Wt % C1 | 3.50 | 3.61 | 3.60 | 3.61 | 3.61 | 3.64 | 3.61 | 3.62 | 3.64 |
| Wt % C4 | 0 | 0.12 | 0.11 | 0.15 | 0.15 | 0.17 | 0.17 | 0.17 | 0.17 |
| Wt % C4+ | 0 | 0.25 | 0.23 | 0.30 | 0.29 | 0.33 | 0.32 | 0.32 | 0.33 |
| % Acet. conversion | — | 80.36 | 78.38 | 89.39 | 90.66 | 99.13 | 99.21 | 99.45 | 99.29 |
| % Sel. to Ethlyene | — | 66.60 | 68.59 | 37.90 | 46.57 | 18.33 | 12.62 | 10.95 | 5.39 |

Figure 2:
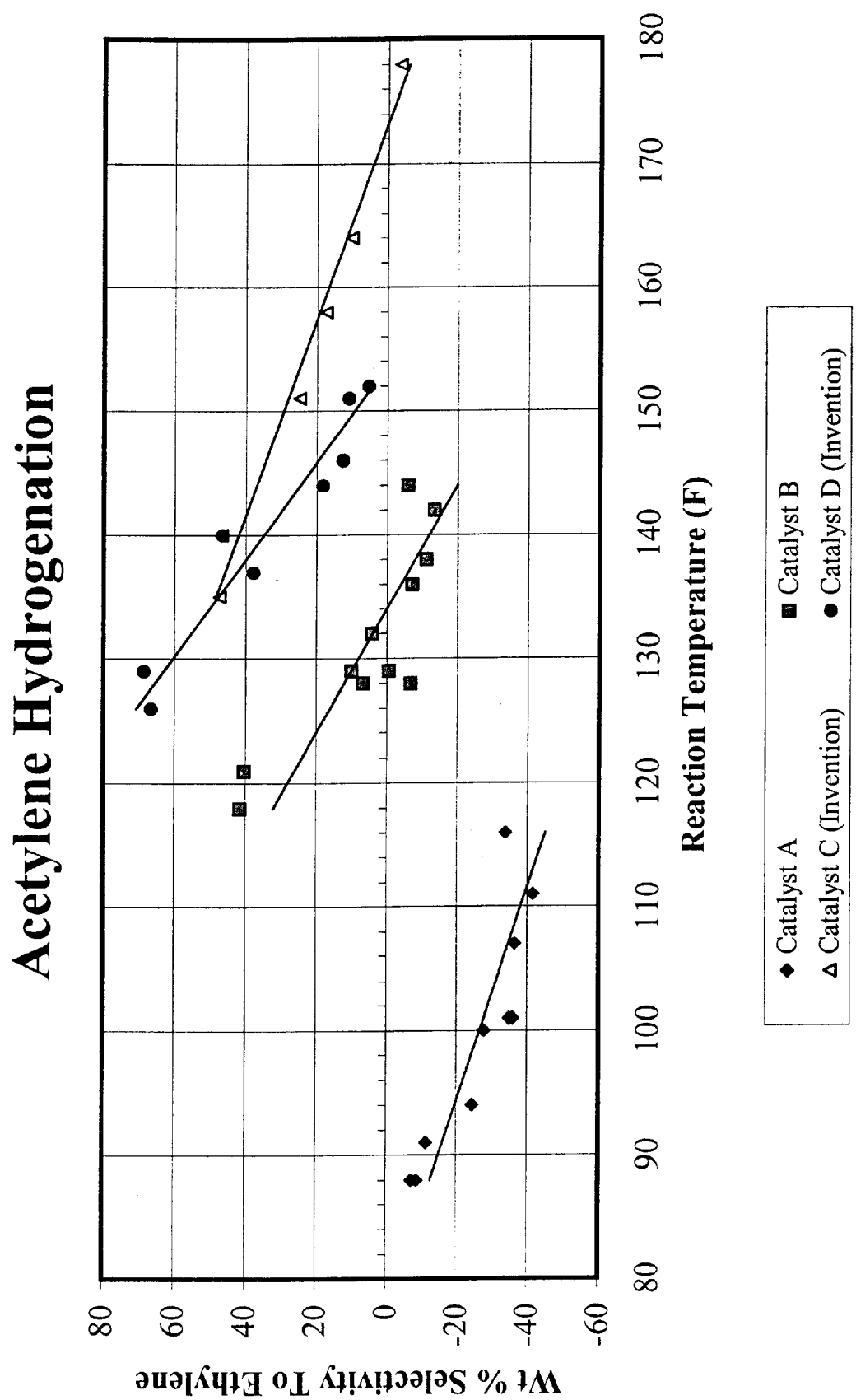
FIG. 2 is a plot of Reaction Temperature versus Weight Percent Selectivity to Ethylene for the catalysts prepared in Example I and employed in the acetylene hydrogenation process of Example II.

FIGS. 1 and 2 plot data from Tables A–D. FIG. 1 illustrates that for a given acetylene conversion value the inventive catalysts provide superior selectivity to ethylene. FIG. 2 illustrates that for a given reaction temperature the inventive catalyst provides superior selectivity to ethylene.

While this invention has been described in detail for the purpose of illustration, it should not be construed as limited thereby but intended to cover all changes and modifications within the spirit and scope thereof.

That which is claimed is:

1. A catalyst composition comprising an inorganic support material, a palladium component, a silver component, and a promoter component, wherein said promoter component has the formula $XYF_n$, wherein X is an alkaline metal, Y is an element selected from the group consisting of antimony and phosphorus, and n is an integer which makes $YF_n$ a monovalent anion.

2. A catalyst composition according to claim 1 wherein X is selected from the group consisting of potassium, rubidium, and cesium and wherein Y is selected from the group consisting of antimony and phosphorus.

3. A catalyst composition according to claim 2 wherein n is an integer from 2 to 8 which makes $YF_n$ a monovalent anion.

4. A catalyst composition according to claim 3 wherein the amount of said promoter component in said catalyst composition is such that the weight of X as a percentage of the total weight of said catalyst composition is from about 0.001 percent to about 10 percent.

5. A catalyst composition according to claim 4 wherein the amount of said palladium component in said catalyst composition is such that the weight of said palladium component as a percentage of the total weight of said catalyst composition is from about 0.001 percent to about 1 percent.

6. A catalyst composition according to claim 5 wherein the amount of said silver component in said catalyst composition is such that the weight of said silver component as a percentage of the total weight of said catalyst composition is from about 0.001 percent to about 5 percent.

7. A catalyst composition according to claim 6 wherein said inorganic support is selected from the group consisting of alumina, titania, zirconia, and mixtures thereof.

8. A catalyst composition according to claim 1 wherein said promoter component is selected from the group consisting of $KSbF_6$, $KPF_6$, and mixtures thereof.

9. A catalyst composition according to claim 8 wherein the amount of said promoter component in said catalyst composition is such that the weight of potassium as a percentage of the total weight of said catalyst composition is from about 0.01 percent to about 2 percent.

10. A catalyst composition according to claim 9 wherein the amount of said palladium component in said catalyst composition is such that the weight of said palladium component as a percentage of the total weight of said catalyst composition is from about 0.005 percent to about 0.2 percent.

11. A catalyst composition according to claim 10 wherein the amount of said silver component in said catalyst composition is such that the weight of said silver component as a percentage of the total weight of said catalyst composition is from about 0.005 percent to about 1 percent.

12. A catalyst composition according to claim 11 wherein said inorganic support is alumina.

13. A catalyst composition according to claim 11 wherein the amount of said promoter component in said catalyst composition is such that the weight of potassium as a percentage of the total weight of said catalyst composition is from 0.05 percent to 1 percent.

14. A catalyst composition according to claim 13 wherein the amount of said palladium component in said catalyst composition is such that the weight of said palladium component as a percentage of the total weight of said catalyst composition is from 0.01 percent to 0.1 percent.

15. A catalyst composition according to claim 14 wherein the amount of said silver component in said catalyst composition is such that the weight of said silver component as a percentage of the total weight of said catalyst composition is from 0.01 percent to 0.5 percent.

16. A catalyst composition according to claim 15 wherein said inorganic support is alpha-alumina.

17. A catalyst composition according to claim 16 wherein said promoter component is $KSbF_6$.

* * * * *

UNITED STATES PATENT AND TRADEMARK OFFICE
CERTIFICATE OF CORRECTION

PATENT NO.   : 6,465,391 B1
DATED        : October 15, 2002
INVENTOR(S)  : Tin-Tack Peter Cheung et al.

It is certified that error appears in the above-identified patent and that said Letters Patent is hereby corrected as shown below:

Column 3,
Line 4, delete "galladium" and insert -- gallium --.
Line 17, delete "promotor" and insert -- promoter --.

Column 4,
Line 20, delete "catalyt" and insert -- catalyst --.

Columns 5 and 6,
Table A, delete "Wt % Ethlylene" and insert -- Wt % Ethylene --.
Table A, delete "% Sel. To Ethylene" and insert -- % Sel. To Ethylene --.

Columns 7 and 8,
Table B, delete "Wt % Ethlylene" and insert -- Wt % Ethylene --.
Table B, delete "% Sel. To Ethylene" and insert -- % Sel. To Ethylene --.
Table C, delete "Wt % Ethlylene" and insert -- Wt % Ethylene --.
Table C, delete "% Sel. To Ethylene" and insert -- % Sel. To Ethylene --.
Table C, delete "% Acet.e conversion" and insert -- % Acet. conversion --.
Table D, delete "Wt % Ethlylene" and insert -- Wt % Ethylene --.
Table D, delete "% Sel. to Ethlylene" and insert -- % Sel. to Ethylene --.

Signed and Sealed this

Fourteenth Day of February, 2006

JON W. DUDAS
*Director of the United States Patent and Trademark Office*